(12) United States Patent
Cardosi et al.

(10) Patent No.: US 10,626,432 B2
(45) Date of Patent: Apr. 21, 2020

(54) ELECTRON TRANSFER AGENT

(71) Applicant: Inside Biometrics Limited, Dingwall (GB)

(72) Inventors: Marco Cardosi, Dingwall (GB); Stephanie Kirkwood, Dingwall (GB)

(73) Assignee: INSIDE BIOMETRICS INTERNATIONAL LIMITED, Dingwall (GB)

( * ) Notice: Subject to any disclaimer, the term of this patent is extended or adjusted under 35 U.S.C. 154(b) by 152 days.

(21) Appl. No.: 15/569,901

(22) PCT Filed: Apr. 28, 2016

(86) PCT No.: PCT/GB2016/051228
§ 371 (c)(1),
(2) Date: Oct. 27, 2017

(87) PCT Pub. No.: WO2016/174455
PCT Pub. Date: Nov. 3, 2016

(65) Prior Publication Data
US 2018/0105856 A1 Apr. 19, 2018

(30) Foreign Application Priority Data
Apr. 30, 2015 (GB) .................................. 1507452.9

(51) Int. Cl.
*G01N 27/327* (2006.01)
*C12Q 1/00* (2006.01)
(Continued)

(52) U.S. Cl.
CPC .......... *C12Q 1/004* (2013.01); *A61B 5/14532* (2013.01); *C07F 15/0053* (2013.01);
(Continued)

(58) Field of Classification Search
CPC .... C12Q 1/004; C12Q 1/005; G01N 27/3272; G01N 27/3271
See application file for complete search history.

(56) References Cited

U.S. PATENT DOCUMENTS

| | | | |
|---|---|---|---|
| 4,942,127 A | 7/1990 | Wada et al. | |
| 7,258,978 B2 * | 8/2007 | Crothers | ................ C12Q 1/682 435/287.2 |

(Continued)

FOREIGN PATENT DOCUMENTS

| | | |
|---|---|---|
| EP | 2821497 A2 | 1/2015 |
| WO | 9613510 A | 5/1996 |

(Continued)

OTHER PUBLICATIONS

EPO computer-generated English language translation.of teh Description section JP 2014-160024 A (Year: 2014).*

(Continued)

*Primary Examiner* — Alexander S Noguerola
(74) *Attorney, Agent, or Firm* — Tarolli, Sundheim, Covell & Tummino LLP

(57) ABSTRACT

A composition is provided. The composition comprises an enzyme and a ruthenium- or osmium-based electron transfer agent, wherein the ruthenium- or osmium-based electron transfer agent is a complex $[M(A)_x(B)_y](X)_n$ wherein M is ruthenium or osmium; A is an amine ligand; each B is a ligand different to A; x is an integer selected from 1 to 5; y is an integer selected from 1 to 5; x+y is 6 or 8; n is an integer selected from 1 to 6; and X is any suitable counterion.

14 Claims, 6 Drawing Sheets

(51) Int. Cl.
*C07F 15/00* (2006.01)
*A61B 5/145* (2006.01)

(52) U.S. Cl.
CPC ......... *C12Q 1/006* (2013.01); *G01N 27/3272* (2013.01); *G01N 2333/904* (2013.01)

(56) References Cited

U.S. PATENT DOCUMENTS 8,303,801 B2 * 11/2012 Wilsey .................. C12Q 1/001
205/792
2004/0194302 A1 10/2004 Bhullar et al.

FOREIGN PATENT DOCUMENTS

| WO | 2006067424 A1 | 6/2006 |
| WO | 2007072018 A2 | 6/2007 |
| WO | 2010035048 A1 | 4/2010 |

OTHER PUBLICATIONS

EPO computer-generated English language translation of the Description section JP 2007-225305 A (Year: 2007).*
Electrochemistry Communications 7 (2005), Sato et al. "Enzyme-based glucose fuel cell using Vitamin K3-immobilized polymer as an electron mediator", pp. 643-647 (Year: 2007).*
International Search Report and Written Opinion dated Aug. 4, 2016 for corresponding International Patent Application No. PCT/GB2016/051228.
GB Search Report dated Feb. 2, 2016 for corresponding GB Patent Application No. 1507452.9.
Salimi, Abdollah et al., Journal of Solid State Electrochemistry, vol. 13(3), pp. 485-496, 2009.
Laliberte, J.F. et al, Journal of Bioenergetics and Biomembranes, vol. 19(1), pp. 69-81, 1987.

* cited by examiner

ELECTRON TRANSFER AGENT

RELATED APPLICATIONS

The present application is a U.S. National Stage application under 35 USC 371 of PCT Application Serial No. PCT/GB2016/051228, filed on 28 Apr. 2016; which claims priority from GB Patent Application No. 1507452.9, filed 30 Apr. 2015, the entirety of both of which are incorporated herein by reference.

TECHNICAL FIELD

The present invention relates to compositions for coating a test strip and test devices comprising these compositions for determining the concentration of an analyte in a fluid sample.

BACKGROUND

The detection and measurement of substances, chemicals, or analytes in a bodily fluid sample is useful in a variety of applications, such as in fitness monitors or in the medical device industry. For example, an individual may choose to monitor a concentration of an analyte such as β-hydroxybutyrate or glycerol in his or her bloodstream in order to determine whether or not a chosen fitness regime is effective. Glycerol is a fitness related analyte associated with lipolysis and fat breakdown from stored body fat.

As another example, people with diabetes need to regularly monitor the concentration of glucose in their bloodstream in order to determine if they are in need of glucose or insulin or other diabetes medication. Diagnostic devices and kits have been developed over the years to allow a diabetic individual to autonomously determine the concentration of glucose in their bloodstream, in order to better anticipate the onset of hyperglycaemia or hypoglycaemia and take any necessary action.

When trying to ascertain a level of an analyte in, for example, a blood sample, an individual will typically perform a finger stick using a lancing device to extract a small drop of blood from a finger or alternative site. An electrochemical test device, which is often a test strip, is then inserted into a diagnostic meter, and the sample is applied to the test strip. Through capillary action, the sample flows through a capillary channel across a measurement chamber of the device and into contact with one or more electrodes or conductive elements coated with sensing chemistry for interacting with a particular analyte or other specific chemical (for example glucose) in the blood sample. The magnitude of the reaction is dependent on the concentration of the analyte in the blood sample. The diagnostic meter may detect the current generated by the reaction of the sensing chemistry with the analyte, and the result can be displayed to the individual.

Typically, such electrochemical test devices have a set of electrodes such as a counter/reference electrode and one or more working electrodes. Sensing chemistry is used which is typically tailored to the particular analyte or biometric of interest. An enzymatic electrode is a combination of an enzyme and an electrochemical transducer. The direct transfer of electrons between the enzyme and the electrode is generally not easy to achieve and so an electron transfer agent (or mediator) is sometimes used to carry electrons between the electrode and the enzyme to facilitate the electrocatalysis. For example, when measuring the concentration of glucose in a sample, a glucose oxidase or a glucose dehydrogenase enzyme can be used in conjunction with a mediator such as potassium ferricyanide. When detecting other analytes, different enzymes may be used, such as β-hydroxybutyrate dehydrogenase for measuring the ketone body β-hydroxybutyrate.

A number of different mediators, or electron transfer agents have been used in enzyme-based electrochemical sensors. Many of these mediators have one of more of the following limitations: they are poorly soluble and/or unstable in test solutions, they do not exchange electrons rapidly enough with the enzyme, electrode, or both. Some of these electron transfer agents also interact with interfering electroactive compounds, which lead to inaccurate measurements.

There is therefore a need for compositions comprising analyte-detecting enzymes and electron transfer agents which can be used as a part of an electrochemical test device and which enable accurate and sensitive analyte measurement.

SUMMARY

Accordingly, in a first aspect, the present invention provides a composition comprising an enzyme and a ruthenium- or osmium-based electron transfer agent, wherein the ruthenium- or osmium-based electron transfer agent is a complex of formula I, $$[M(A)_x(B)_y](X)_n \quad \text{Formula I}$$

wherein
M is ruthenium or osmium;
A is an amine ligand;
Each B is a ligand different to A;
x is an integer selected from 1 to 5;
y is an integer selected from 1 to 5;
x+y is 6 or 8;
n is an integer selected from 1 to 6;
X is any suitable counterion.

In a second aspect, the present invention provides a composition comprising a diaphorase and a ruthenium- or osmium-based electron transfer agent.

The compositions of the present invention are effective in electrochemical sensors. More specifically, the combination of the enzyme and the transition metal complex of the present invention have a lower redox potential which results in less interference from interfering electroactive substances in an analyte sample, for example uric acid.

In a third aspect, the present invention provides an electrochemical test device for determining a concentration of an analyte in a fluid sample, the electrochemical test device comprising a set of electrodes including a working electrode and sensing chemistry for the working electrode, wherein the sensing chemistry comprises a diaphorase and a ruthenium- or osmium-based electron transfer agent.

In a fourth aspect, the present invention provides an electrochemical test device for determining a concentration of an analyte in a fluid sample, the electrochemical test device comprising a set of electrodes including a working electrode and sensing chemistry for the working electrode, wherein the sensing chemistry comprises a ruthenium- or osmium-based electron transfer agent, wherein the ruthenium- or osmium-based electron transfer agent is a complex of formula I $$[M(A)_x(B)_y](X)_n \quad \text{Formula I}$$

wherein

M is ruthenium or osmium;

A is an amine ligand;

Each B is a ligand different to A;

x is an integer selected from 1 to 5;

y is an integer selected from 1 to 5;

x+y is 6 or 8;

n is an integer selected from 1 to 6;

X is any suitable counterion.

In a fifth aspect, the present invention provides a process for preparing [Ru$^{III}$(NH$_3$)$_5$(pyridine)].2(PF$_6$), the process comprising treatment of [Ru$^{II}$(NH$_3$)$_5$Cl].2Cl with zinc amalgam and pyridine; treatment of the resulting product with ammonium hexafluorophosphate; and oxidation to [Ru$^{III}$(NH$_3$)$_5$(pyridine)].2(PF$_6$).

In a sixth aspect, the present invention provides a process for preparing [Ru$^{III}$(NH$_3$)$_5$(4-methyl pyridine)].2(PF$_6$), the process comprising treatment of [Ru$^{II}$(NH$_3$)$_5$Cl].2Cl with zinc amalgam and 4-methyl pyridine; treatment of the resulting product with ammonium hexafluorophosphate; and oxidation to [Ru$^{III}$(NH$_3$)$_5$(4-methyl pyridine)].2(PF$_6$).

In a seventh aspect, the present invention provides a composition, test device, process as substantially described herein with reference to or as illustrated in one or more of the examples or accompanying figures.

Other aspects and features of the present invention will be appreciated from the following description and the accompanying claims.

BRIEF DESCRIPTION OF THE DRAWINGS

Illustrative embodiments of the present disclosure will now be described, by way of example only, with reference to the drawings. In the drawings.

DESCRIPTION

Figure 1:
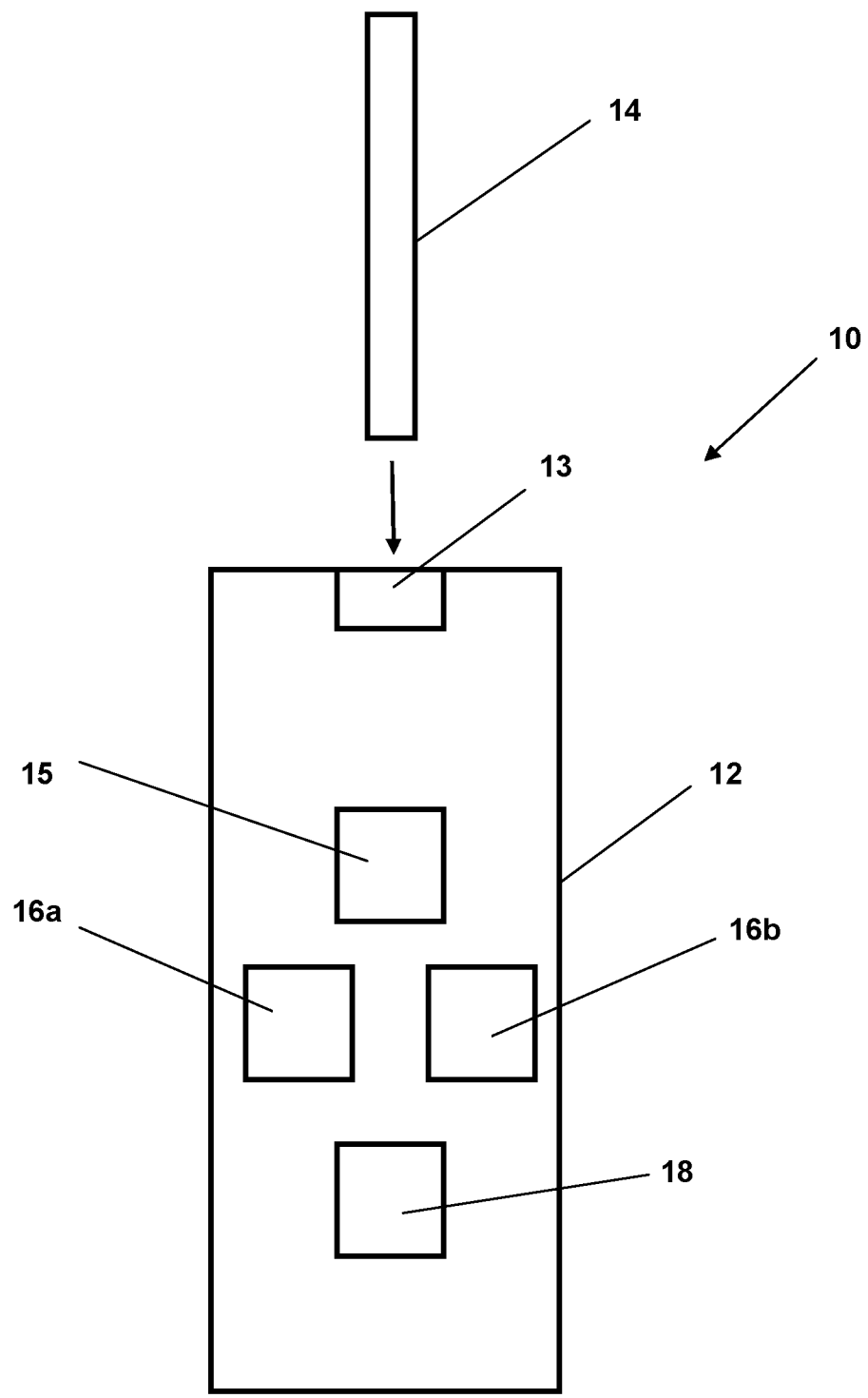
FIG. 1 shows a strip-meter system.

The term "alkyl", used alone or as part of a larger moiety, refers to a straight and branched chain aliphatic group having from 1 to 12 carbon atoms. The alkyl group therefore has 1, 2, 3, 4, 5, 6, 7, 8, 9, 10, 11 or 12 carbon atoms. For purposes of the present invention, the term "alkyl" will be used when the carbon atom attaching the aliphatic group to the rest of the molecule is a saturated carbon atom. However, an alkyl group may include unsaturation at other carbon atoms. Thus, alkyl groups include, without limitation, methyl, ethyl, propyl, allyl, propargyl, butyl, pentyl, and hexyl.

The term "amine" may refer to a primary, secondary or tertiary amine. The amine will generally be NRR'R", where R, R' and R" are each selected from hydrogen or alkyl. Any suitable alkyl group may be used. The alkyl group may be C$_1$, C$_2$, C$_3$, C$_4$, C$_5$, or C$_6$. The amine may be NH$_3$.

The term "heteroaryl" means a monocyclic or bicyclic radical of 5 to 12 ring atoms having at least one aromatic ring containing one, two, or three ring heteroatoms selected from N, O or S, the remaining ring atoms being C. The attachment point of the heteroaryl radical may be via the heteroatom. The heteroaryl rings may be optionally substituted as defined herein. Examples of heteroaryl moieties include, but are not limited to, optionally substituted imidazolyl, oxazolyl, isoxazolyl, thiazolyl, isothiazolyl, oxadiazolyl, thiadiazolyl, pyrazinyl, thienyl, benzothienyl, thiophenyl, furanyl, pyranyl, pyridyl, pyrrolyl, pyrazolyl, pyrimidyl, quinolinyl, isoquinolinyl, benzofuryl, benzothiophenyl, benzothiopyranyl, benzimidazolyl, benzooxazolyl, benzooxadiazolyl, benzothiazolyl, benzothiadiazolyl, benzopyranyl, indolyl, isoindolyl, triazolyl, triazinyl, quinoxalinyl, purinyl, quinazolinyl, quinolizinyl, naphthyridinyl, pteridinyl, carbazolyl, azepinyl, diazepinyl, acridinyl and the like, including partially hydrogenated derivatives thereof.

The term "halide" refers to a substituent which is fluoro, chloro, bromo or iodo.

The term "substituted", as used herein, means that a hydrogen radical of the designated moiety is replaced with the radical of a specified substituent, provided that the substitution results in a stable or chemically feasible compound. The phrase "one or more substituents", as used herein, refers to a number of substituents that equals from one to the maximum number of substituents possible based on the number of available bonding sites, provided that the above conditions of stability and chemical feasibility are met. Unless otherwise indicated, an optionally substituted group may have a substituent at each substitutable position of the group, and the substituents may be either the same or different.

Throughout this specification, reference is made to directional terms such as "above" and "below", or "upper" and "lower". References made to such terms are purely indicative of relative positions of the features of embodiments disclosed herein. For example, wherever there is mention of a cover above a spacer layer and an insulator layer below the spacer layer, it should be understood that the cover and the insulator layer are formed on opposite sides of the spacer layer. That is, directional terms such as those described herein do not refer to a direction relative to a viewpoint of an observer, but instead should be considered in all aspects as relative terms.

An electron transfer agent (or redox mediator) is an agent for transferring electrons between an analyte or an analyte-reduced or analyte-oxidized enzyme and an electrode, either directly, or via one or more additional electron transfer agents.

The ruthenium- or osmium-based electron transfer agent is a complex of formula I:

$$[M(A)_x(B)_y](X)_n \qquad \text{Formula I}$$

M is a transition metal. M may be ruthenium or osmium. M may be ruthenium. M may be Ru(II) or Ru(III).

The oxidation state of the metal M in the complex may be selected to be 2+, 3+ or 4+. The oxidation state of the metal M in the complex of formula I may be 3+.

A is an amine ligand. A may be NRR'R", wherein R, R' and R" are independently selected from hydrogen or alkyl. A may be NH$_3$. It will be appreciated that when x is two or more, all "A" may be the same.

Each B is a ligand different to A. It will be appreciated that when y is 2 or more, B may be the same or different. B may be independently selected from a halide or optionally substituted heteroaryl. B may be a halide, preferably wherein the halide is selected from the group consisting of F$^-$, Cl$^-$, Br$^-$, I$^-$. B may be chloride. B may be pyridyl, or 4-methyl pyridyl.

x may be an integer selected from 1, 2, 3, 4, or 5.

y may be an integer selected from 1, 2, 3, 4 or 5.
x+y is 6 or 8.
n is an integer selected from 1, 2, 3, 4, or 5.

It will be appreciated that A and B may be selected such that the overall charge on the complex of formula I is selected from the group +2, +1, 0, −1, −2 and −3.

The ruthenium complex may be selected from [Ruthenium$^{III}$(NH$_3$)$_5$Cl]X, [Ruthenium$^{III}$(NH$_3$)$_5$(pyridine)]X, and [Ruthenium$^{III}$(NH$_3$)$_5$(4-methyl pyridine)]X.

The counterion X may be a counterion selected to lead to the charge neutrality of [M(A)$_x$(B)$_y$]. The counterion X may be selected from F$^-$, Cl$^-$, Br$^-$, I$^-$, PF$_6^-$.

In a particularly preferred aspect of the first aspect of the invention, there is provided a ruthenium complex selected from: [Ruthenium$^{III}$(NH$_3$)$_5$Cl].2Cl, [Ruthenium$^{III}$(NH$_3$)$_5$(pyridine)].3PF$_6$, [Ruthenium$^{III}$(NH$_3$)$_5$(4-methyl pyridine)].3Cl.

[Ruthenium$^{III}$(NH$_3$)$_5$(pyridine)].3PF$_6$ may be prepared by the treatment of [Ru$^{II}$(NH$_3$)$_5$Cl].2Cl with zinc amalgam and pyridine. The resulting product may be treated with ammonium hexafluorophosphate. This reduced product may then be oxidized to [Ru$^{III}$(NH$_3$)$_5$(pyridine)].2(PF$_6$). Oxidation to [Ru$^{III}$(NH$_3$)$_5$(pyridine)].2(PF$_6$) may take place using silver oxide.

[Ruthenium$^{III}$(NH$_3$)$_5$(4-methyl pyridine)].3Cl may be prepared by the treatment of [Ru$^{II}$(NH$_3$)$_5$Cl].2Cl with zinc amalgam and 4-methyl pyridine. The resulting product may be treated with ammonium hexafluorophosphate. The reduced product may then be oxidized to [Ru$^{III}$(NH$_3$)$_5$(4-methyl pyridine)].2(PF$_6$). Oxidation to [Ru$^{III}$(NH$_3$)$_5$(4-methyl pyridine)].2(PF$_6$) may take place using silver oxide.

Transition metal complexes of the present invention may be soluble in water or other aqueous solutions. In general, the transition metal complexes may be made soluble in aqueous solvents by having an appropriate counterion or ions, X. The solubility of the transition metal complex of the present invention may be greater than about 0.025M at 25° C. in water.

Enzymes for use in this invention may be diaphorase, glucose oxidase.

The diaphorase may be any suitable diaphorase. The diaphorase may be a member of the class of flavin-bound enzymes that catalyse the reduction of compounds which act as hydrogen acceptors from the reduced form of di- and tri-phosphopyridine nucleotides, i.e. NADH or NADPH. For example, the diaphorase may be an NADPH:acceptor oxidoreductase (NADPH dehydrogenase of the class EC 1.6.99.1). The diaphorase may be an NADH:acceptor oxidoreductase (NADH dehydrogenase of the class EC 1.6.99.3). The diaphorase may be an NADH:(quinone acceptor) oxidoreductase (NADH dehydrogenase (quinone) of the class EC 1.6.99.5).

The composition may comprise between about 0.3%-2% (w/w) enzyme. The enzyme may be diaphorase. The composition may comprise about 1% (w/w) diaphorase.

The composition may comprise about 2%-5% (w/w) glucose oxidase. The composition may comprise about 4% (w/w) glucose oxidase.

The solution for dissolving the enzyme may comprise a buffer such as, for example, phosphate, citrate, piperazine-N,N'-bis(2-ethanesulfonic acid) (PIPES) and diethanolamine HCl or Tris buffer. The pH of the buffer, where the enzyme is diaphorase, may be about 7.

The composition may comprise a phosphate or Tris buffer. The pH of the buffer may be in the range of about 6.5-7.5. The pH of the buffer may be about 7.

The enzyme may comprise an enzyme activity range of from about 50 kilounits (kU) per 100 grams composition to about 1500 kU. The enzyme activity range is selected so that the analyte current does not depend on the level of enzyme activity in the composition and to avoid solubility issues for too high levels of enzyme. The diaphorase may have an enzyme activity range of from about 75 kU to 200 kU per 100 grams composition. The diaphorase activity is measured spectrophotometrically either by coupling the enzyme reaction to a dye or by measuring the conversion of NADH to NAD+ at 340 nm. The glucose oxidase may have an enzyme activity range of from about 500 kU to about 1300 kU per 100 grams. Glucose oxidase activity is measured using methods known in the art, in particular using an oxygen electrode and monitoring the rate of oxygen reduction.

The composition may comprise between about 8%-15% (w/w) of an electron transfer agent. Preferably, the electron transfer agent is a ruthenium-based electron transfer agent. Preferably, the composition comprises 10% (w/w) electron transfer agent.

The composition may comprise between about 0.07%-0.13% (w/w) flavin mononucleotide (FMN). Preferably, the composition comprises 0.1% (w/w) FMN.

The composition may comprise about 0.5%-3.5% (w/w), or 2.5%-3.5% (w/w), hydroxyethyl cellulose (HEC). Preferably, the composition comprises 3% HEC.

A fluid sample may be a biological fluid. For example, the biological fluid may be blood, interstitial fluid, plasma, sweat, lachrymal fluid, or breath condensate. The analyte may be an analyte found in the fluid sample. For example, the analyte may be glucose, lactate, glycerol, cholesterol, or a ketone such as β-hydroxybutyrate.

The ruthenium- or osmium-based electron transfer agent may have a standard oxidation potential in the range of between about −0.52 to 0.35 V. The ruthenium- or osmium-based electron transfer agent may have a standard oxidation potential in the range of between about −0.52 to 0.18 V. The standard oxidation potential is measured using a standard hydrogen electrode (SHE) at standard temperature (25° C.) and pressure (1 atm).

An electrochemical test device is disclosed for determining a concentration of an analyte in a fluid sample. The electrochemical test device comprises a set of electrodes including a working electrode and sensing chemistry for the working electrode. The sensing chemistry comprises a diaphorase. The sensing chemistry further comprises a ruthenium- or osmium-based electron transfer agent. The electron transfer agent is for facilitating the transfer of electrons from the analyte to the working electrode.

In another embodiment, an electrochemical test device is disclosed for determining a concentration of an analyte in a fluid sample. The electrochemical test device comprises a set of electrodes including a working electrode and sensing chemistry for the working electrode. The sensing chemistry comprises a ruthenium- or osmium-based electron transfer agent. The electron transfer agent is for facilitating the transfer of electrons from the analyte to the working electrode.

Sensing chemistry typically comprises at least one reagent which interacts with an analyte in the fluid sample to produce, directly or indirectly, a detectable signal at the working electrode for the analyte. When producing the signal indirectly more than one reagent is usually involved.

The electrochemical test device may further comprise an NAD(P)$^+$-dependent dehydrogenase and a cofactor for the NAD(P)$^+$-dependent dehydrogenase.

The cofactor may be nicotinamide adenine dinucleotide (NAD+). The cofactor may be nicotinamide adenine dinucleotide phosphate (NADP+).

The NAD(P)$^+$-dependent dehydrogenases may be Glycerol dehydrogenase, Glycerol-3-phosphate dehydrogenase, D-3-Hydroxybutyrate dehydrogenase, Glucose Dehydrogenase (NAD Dependent), Cholesterol Dehydrogenase, Lactate Dehydrogenase, D-Lactate dehydrogenase, Malate Dehydrogenase, Alcohol Dehydrogenase or Leucine dehydrogenase.

The sensing chemistry may further comprise glucose oxidase.

The sensing chemistry may comprise an NAD(P)H detection layer. The NAD(P)H detection layer may comprise a diaphorase.

The sensing chemistry may comprise an analyte sensitive layer, which is suitable for detection of an analyte. For example, the analyte sensitive layer may comprise an NAD(P)$^+$-dependent dehydrogenase and cofactor.

The electrochemical test device may comprise an analyte selective layer comprising NAD(P)$^+$-dependent dehydrogenase for reacting with an analyte and a NAD(P)H detection layer comprising a diaphorase.

The sensing chemistry may be disposed on the working electrode in layers including a layer adjacent the working electrode. There may be two layers. The layer adjacent the working electrode may comprise the diaphorase. The layer adjacent the electrode may also comprise the electron transfer agent.

By disposing sensing chemistry in layers upon the working electrode, particular requirements of the NAD(P)$^+$-dependent dehydrogenase and the diaphorase can be addressed more efficiently for optimal performance by altering the makeup of individual layers. For example, the pH level of a particular layer may be altered using suitable buffer components or otherwise in order to optimize the performance of the NAD(P)$^+$-dependent dehydrogenase and the diaphorase.

The layers may include a layer which is not adjacent the working electrode. The layer which is not adjacent the working electrode may comprise the NAD(P)$^+$-dependent dehydrogenase.

The layer not adjacent the electrode may also comprise the cofactor. By providing the cofactor only in the layer not adjacent the electrode, the background noise of the analyte measurement is reduced, further improving the sensitivity of the electrochemical test device. Furthermore, by providing the cofactor only in the layer not adjacent the electrode, the production process of the electrochemical test devices is greatly simplified and the reagents are used efficiently. Furthermore, by providing the cofactor in the same layer as the NAD(P)$^+$-dependent dehydrogenase, the diffusion distances between the cofactor and the dehydrogenase are reduced. Accordingly, there is an improvement to the electrode response and performance when measuring an analyte in a fluid sample.

In the context used herein, "about" may refer to a variation of ±10% of the numerical value. All preferred features of each of the aspects of the invention apply to all other aspects mutatis mutandis.

The following electron transfer agents were prepared: [Ru$^{III}$(NH$_3$)$_5$Cl].2Cl, [Ru$^{III}$(NH$_3$)$_5$(pyridine)].3PF$_6$, [Ru$^{III}$(NH$_3$)$_5$(4-methyl pyridine)].3PF$_6$.

All reactions were conducted under argon atmosphere. All solvents and reagents were obtained from commercial sources (Aldrich, Carlo-Erba, Fischer).

Preparation of [Ru$^{III}$(NH$_3$)$_5$Cl].2Cl

To a 5 L round bottom flask fitted with an overhead stirrer was added ruthenium (III) hexaammine trichloride (50 g, 0.1614 moles) in 280 mL deionized water. The mixture was stirred to dissolve at room temperature. A solution of 6M HCl (180 mL concentrated HCl+180 ml water) was added slowly to the reaction flask and heated to reflux for 3 hours. The solution was allowed to cool before placing in a freezer overnight. The solid product obtained was collected via filtration under vacuum. The crude product was recrystallized by first redissolving the solid in 650 mL deionized water and 70 mL concentrated HCl under reflux. The hot liquid was filtered to remove undissolved impurities. Concentrated HCl (300 mL) was added to the filtrate to precipitate a yellow-orange solid which was collected by filtration and washed with ethanol (100 mL) and diethyl ether (100 mL) and dried in a vacuum oven at 50° C. overnight to yield the product as an orange solid powder (26.3 g).

Preparation of [Ru$^{II}$(NH$_3$)$_5$(pyridine)].2PF$_6$

Zinc/mercury amalgam was prepared by first stirring zinc powder (21 g) in 2 M HCl. The 2 M HCl was decanted and replaced with 400 ml 0.1 M HCl. Mercuric (II) chloride (51.9 g) was added, and after 5 minutes, the acid was decanted and the Zn/Hg amalgam was washed in deionised water and ethanol. The resulting amalgam was added to a solution of [Ru$^{II}$(NH$_3$)$_5$Cl].2Cl (5.26 g, 0.018 mol) in 400 ml water, and 7-12 drops of trifluoroacetic acid were added and the solution stirred for 30 minutes. The resulting yellow solution was added to pyridine (2.1 ml, 0.027 mol) dissolved in 50 mL deionised water, and left to stir for 3 days. The resulting orange solution was evaporated to remove 180 ml solvent. A saturated aqueous solution of ammonium hexafluorophosphate was added to the ruthenium solution over a period of 50 minutes to result in the formation of a yellow precipitate. The resulting precipitate was collected via filtration and washed with ethanol and diethyl ether to yield the crude product (4.23 g) as a yellow solid. The crude product (2.62 g) was purified by dissolving in 15-20 ml acetone and placed in the freezer overnight to provide an orange solid precipitate and red-coloured supernatant. The precipitate was filtered and dried under vacuum at 40° C. overnight. Diethyl ether (~10 mL) was added to the supernatant to induce precipitation, and the flask was placed in the freezer over 3 days. The resulting precipitate was isolated by filtration and vacuum dried in an oven at 40° C. for 4 hours to yield 1.12 g, 0.002 moles (11.2% yield) of the titled product as a yellow solid.

$\delta_H$ (500 MHz, d$^6$ acetone) 8.2 (2H, d, J=6.3 Hz, C$_6$H$_5$N, H$_1$), 7.7 (1H, t, J=6.5 Hz, C$_4$H$_5$N, H$_2$), 7.3 (2H, t, J=6.5 Hz, C$_5$H$_5$N, H$_3$), 3.0 (3H, s, NH$_3$-trans), 2.8 (s, H$_2$O), 2.6 (12H, s, NH$_3$-cis). Anal. Calc. for Ru.C$_5$H$_{20}$N$_{10}$P$_2$F$_{12}$.H$_2$O: C, 10.82; H, 3.63; N, 15.14. Found: C, 16.08; H, 3.22; N, 11.98.

Preparation of Ru$^{III}$(NH$_3$)$_5$(pyridine).3PF$_6$

To a 500 mL 3-necked round bottom flask was added silver oxide (3.6 g) in water (100 mL), followed by trifluoroacetic acid (~3 mL) dropwise until the silver was solvated forming a clear solution. [Ru$^{II}$(NH$_3$)$_5$(pyridine)].2PF$_6$ was added slowly to the silver solution and stirred at room temperature to yield an orange/yellow solution with a silver metallic precipitate. The silver material was filtered off at a water pump, and the product was precipitated with ammonium hexafluorophosphate solution. The yellow solid obtained by filtration was washed with ethanol (10 mL) and water (10 mL) and dried under vacuum overnight to yield 0.25 g product.

Preparation of [Ru$^{II}$(NH$_3$)$_5$(4-methyl pyridine)].2PF$_6$

[Ru$^{II}$(NH$_3$)$_5$Cl].2Cl (16.2 g, 0.0553 mol) was added to a 1 L three-necked round bottom flask under argon and 650 ml of deionised water was added and the solution was stirred for 30 minutes until fully solvated to provide a yellow solution.

In a 500 ml conical flask zinc powder 3.59 g) in 2 M HCl (200 ml×2) was added and stirred for 10 minutes. The 2 M HCl was decanted off and replaced with 0.1 M HCl (400 mL). Mercuric (II) chloride (5.6 g) was added to the flask and stirred for 5 minutes. The acid was decanted off and the resulting Zn/Hg amalgam was washed in deionised water then ethanol to provide clean Zn/Hg amalgam. The clean Zn/Hg amalgam was added to the round bottom flask containing ruthenium chloropentaammine dichloride along with 7-12 drops of trifluoroacetic acid, and then stirred under argon for 30 minutes.

In a 1 L three-necked round bottom flask, 4-methyl pyridine (10.77 ml, 0.1107 mol) was dissolved in 50 ml deionised water and stirred for 30 minutes to provide a clear solution. The yellow ruthenium solution was added under argon to the ligand solution and left to stir for 3 days under argon. The resulting red-orange reaction mixture was transferred to a 1 L evaporation flask and ~180 mL solvent was removed at 45° C. A saturated solution of 25 mL distilled water and excess ammonium hexafluorophosphate was added to the concentrated reaction mixture over 50 minutes to yield a yellow precipitate which was collected by filtration at a water pump using a frit. The precipitate was washed with ethanol (2×100 mL) followed by diethyl ether (3×100 mL) to yield 13.5 g yellow solid.

Preparation of Ru$^{III}$(NH$_3$)$_5$(4-methyl pyridine).3PF$_6$

To a 500 mL 3-necked round bottom flask was added silver oxide (3.6 g) in water (100 mL), followed by trifluoroacetic acid (~3 mL) dropwise until the silver was solvated forming a clear solution. [Ru$^{II}$(NH$_3$)$_5$(4-methyl pyridine)].2PF$_6$ was added slowly to the silver solution and stirred at room temperature to yield an orange solution with a silver metallic precipitate. The silver material was filtered off at a water pump, and the product was precipitated with ammonium hexafluorophosphate solution. The yellow solid obtained by filtration was washed with ethanol (10 mL) and water (10 mL) and dried under vacuum overnight to yield 0.110 g product.

FIG. 1 shows an apparatus in the form of a strip meter system 10. System 10 comprises a meter 12 for receiving an output signal from an electrochemical test device such as electrochemical test strip 14. Electrochemical test strip 14 comprises a set of electrodes which typically comprises one or more working electrodes (not shown in FIG. 1) and a counter/reference electrode, each of the working electrodes provided with sensing chemistry for reacting with at least one analyte of a fluid sample to be applied to electrochemical test strip 14. In this example, each of the one or more working electrodes has reagents coated thereon. The counter/reference electrode may also have reagents coated thereon. Meter 12 comprises receiving means 13 for receiving electrochemical test strip 14 and applying a potential difference to the working electrode(s) and the counter/reference electrode.

Meter 12 further comprises processing circuitry 15 for carrying various functions relating to the operation of meter 12. For example, processing circuitry 15 is configured to control operation of receiving means 13 so as to control application of a potential difference between the working electrode(s) and the counter/reference electrode. Processing circuitry 15 is further configured to process one or more output signals generated at test strip 14 and to control a display of messages on display 18. The processing circuitry may perform other functions. Meter 12 further comprises first and second memory storages 16a and 16b. Although two memory storages are shown, in other embodiments the memory storages may be combined to form a single memory storage, or meter 12 may comprise more than two memory storages. Meter 12 also comprises a display 18 for displaying readouts of measurements taken by meter 12.

When manufacturing an electrochemical test device such as electrochemical test strip 14 the device can be constructed in layers with different layers providing different features such as conductive tracks, electrode area definition and positioning of chemistry. Suitable manufacturing techniques may be used such as deposition techniques (e.g. printing such as screen printing) and adherence of layers, as will be apparent from the following.

Figure 2:
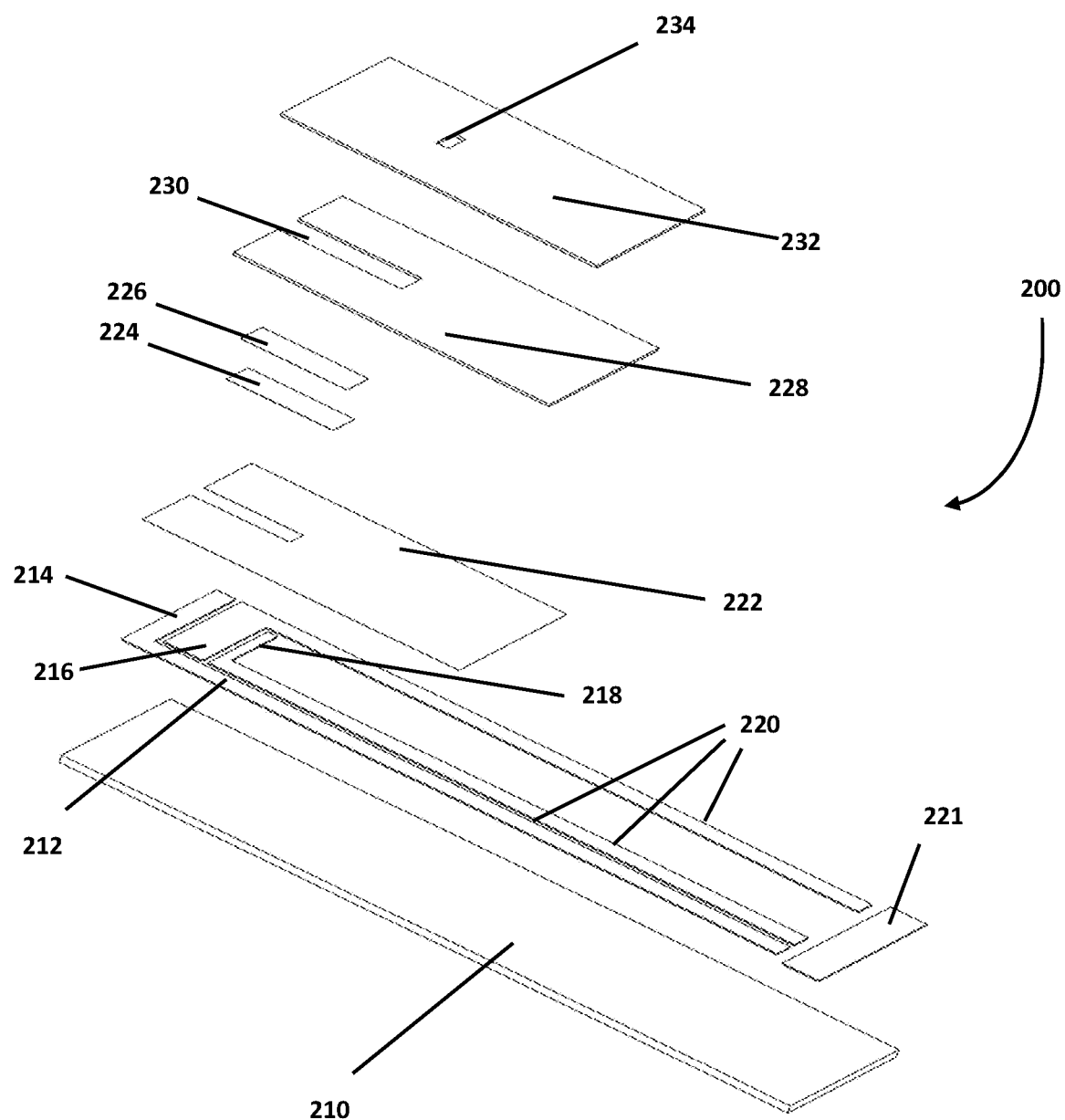
FIG. 2 shows an exploded view of an electrochemical test device.

FIG. 2 shows a perspective, exploded view of an electrochemical test device in the form of electrochemical test strip 200 according to a first example. This example will be described in relation to a received blood sample, although the electrochemical test strip could be used with any suitable fluid sample. The electrochemical test strip shown in FIG. 2 has an end-fill configuration i.e. the blood sample can be received at one end of the electrochemical test device 200.

The electrochemical test strip 200 comprises a support layer or substrate 210. Substrate 210 has a thickness of around 0.35 mm. The substrate 210, in this example, is made from polyester, although any suitable substrate may be used. The substrate 210 is thermally and dimensionally stable, with consistent properties such as thickness, surface roughness and surface energy.

Above the substrate 210 is the conductor layer 212. In this example, the conductor layer 212 is directly disposed upon the substrate 210 using carbon-based ink. In this example, the conductor layer 212 is printed directly onto the upper surface of the substrate 210. The conductor layer 212 may be printed onto the substrate 210 using screen printing, lithographic printing, tomographic printing, sub-microlitre controlled volume drop on demand printing technologies or any other suitable method of printing. The conductor layer comprises a set of electrodes including working electrode 214, counter/reference electrode 216 and fill-sufficiency detect electrode 218. The conductor layer 212 further comprises a set of conductive tracks 220. In this example, the conductive tracks 220 extend along the longitudinal axis of the electrochemical test strip 200. The conductive tracks are suitable for electrically coupling the electrodes to a meter 12. The conductor layer 212 further comprises a switch-on bar 221 for activating a meter 12.

Above the conductor layer 212 is an insulating layer 222. The insulator layer 222 is made of an electrically insulating material, and is directly disposed upon the upper surface of the conductor layer 212. The insulator layer 222 is, in this example, made of a dielectric material and defines an interaction area. That is, the insulation layer 222 electrically insulates some portions of the conductor layer 212 from the layers situated above in the electrochemical test strip 200. Specially designed gaps in the insulator layer 222 expose some portions of the conductor layer 212 to the layers situated above in the electrochemical test strip 200.

Sensing chemistry is applied to the electrodes of the conductor layer 212. In this example, the sensing chemistry comprises two reagent layers 224 and 226 which are applied to exposed electrode interaction areas after the insulator layer 222 is formed. The reagent layers 224 and 226 coat the exposed electrode interaction areas. In this way, the insulator layer 222 defines which part or parts of the electrodes of the conductor layer 212 are able to come into contact with an applied blood sample for the measurement of the analyte.

Above the insulator layer 222 is a spacer layer 228 formed of a polyester core. The spacer layer 228 defines a sample introduction channel 230, or measurement chamber, for introducing a blood sample to the conductor layer 212. The height of the sample introduction channel 230 is defined by the thickness of the spacer layer 228. The spacer layer 228 is formed of double sided adhesive tape which, in this example, is applied directly to the upper surface of the insulator layer 222. The sample introduction channel 230 is formed by providing a gap into the double sided adhesive tape of the spacer layer 228. The thickness of the spacer layer 228 is approximately 0.1 mm, which provides a good balance between the volume of the sample introduction channel and the performance of the electrochemical test strip 200.

Above the spacer layer 228 is a cover layer 232. During manufacture, the spacer layer 228 and the cover layer 232 may be applied to the test strip 200 separately or as a single prelaminated layer, although in this example the cover layer 232 is a separate layer to the spacer layer 228. The cover layer 232 acts as a ceiling to the sample introduction channel 230, thereby substantially closing the sample introduction channel 230 from above. The cover layer 232 is formed of single sided tape and, in this example, is adhered directly to the upper surface of the spacer layer 228. The lower surface of the cover layer 232 has hydrophilic properties, which assist in drawing a blood sample into the sample introduction channel 230. The cover layer 232 further has a vent 234 suitable for venting air out of the sample introduction channel 230 to allow a blood sample to enter the sample introduction channel 230 via capillary action. The vent 234 is narrower than the sample introduction channel 230 so that air may easily vent from the sample introduction channel 230 but blood or any other fluid will not easily be able to pass through the vent 234.

In use, a fluid sample is provided to the electrochemical test device and a potential difference is applied across the fluid sample to generate a detectable output signal indicative of an analyte concentration in the fluid sample. In this example, in use a blood sample is applied to the sample introduction channel 230 of the electrochemical test strip 200. Through capillary action, the blood is drawn into the sample introduction channel 230 to the electrodes 214 and 216 of the conductor layer 212. That is, the sample introduction channel 230 acts as a capillary channel. A potential difference is applied across the electrodes 214 and 216 and the blood sample, and an output signal such as a transient current is generated from the blood sample. The characteristics of the output signal can be used to determine the concentration of an analyte, such as glucose, glycerol or β-hydroxybutyrate, in the blood sample.

Figure 3:
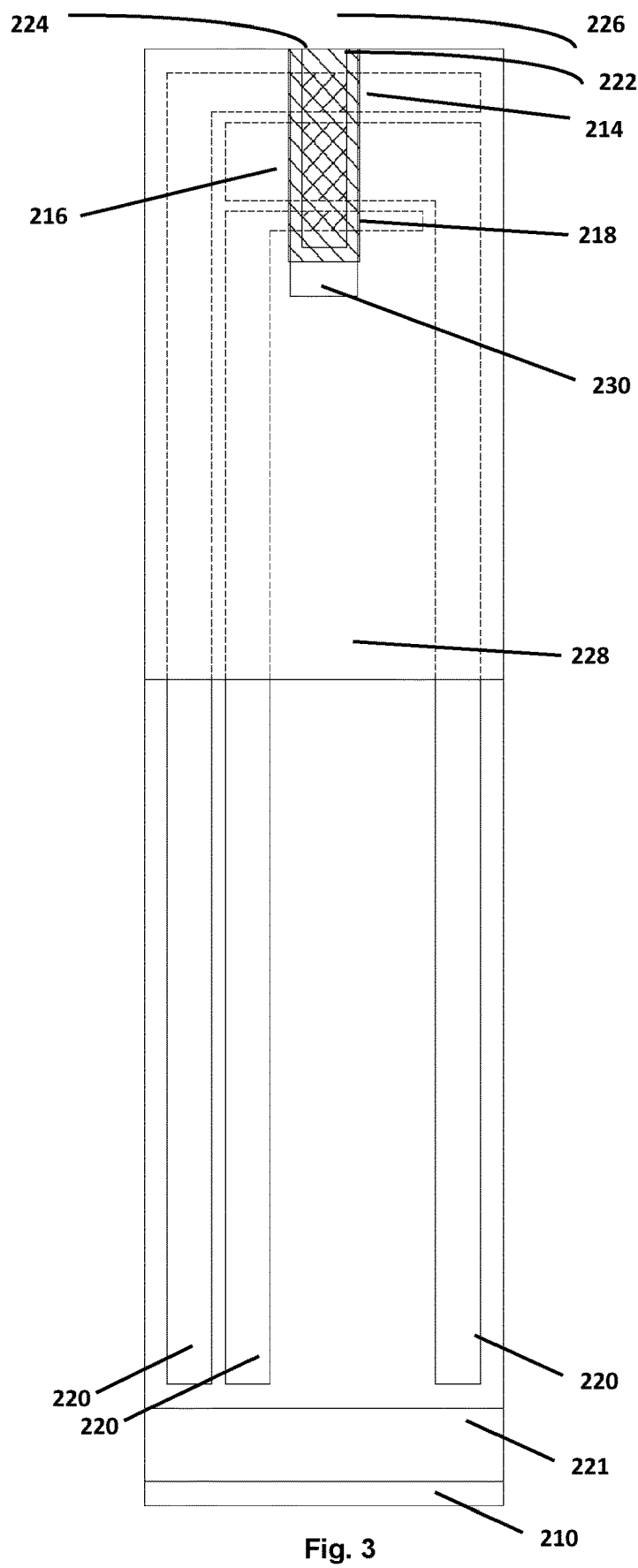
FIG. 3 shows a plan view of some layers of an electrochemical test device.

FIG. 3 depicts a plan view of some of the layers of the electrochemical test strip 200 of FIG. 2. In particular, FIG. 3 shows the substrate 210, the conductor layer 212, the insulator layer 222, the reagent layers 224 and 226, and the spacer layer 228. The cover layer 232 is not shown in FIG. 3 for clarity. The two reagent layers 224 and 226 are applied to the exposed areas of each of the working electrode 214, the counter/reference electrode 216 and the fill-sufficiency detect electrode 218.

Variations of the described embodiments are envisaged, for example, the features of all the disclosed embodiments may be combined in any way.

For example, an electrochemical test device may contain more layers than those disclosed in the preceding description. For example, an electrochemical test device may further comprise one or more bonding layers for bonding together one or more of the layers disclosed above. Additionally, some of the layers are not always necessary. For example, the insulator layer may be absent from the examples discussed above. The spacer layer may define the interaction area of the electrodes of the conductor layer beneath. The spacer layer may perform the dual role of receiving a fluid sample through a capillary channel and defining an interaction area for combining the fluid sample with the conductor layer. For example, the spacer layer can, with appropriate adhesive, define the active area/interaction area of the electrodes.

In the examples discussed above, a layer structure has been shown. The order in which each of the layers is formed may vary and any layer may, in some way, be configured so as to be in contact with any other layer.

The electrochemical test device may be any suitable electrochemical test device. The electrochemical test device may be a test strip. In some examples the electrochemical test device may comprise a patch. Electrochemical test devices such as patches typically comprise a subcutaneous fluid extraction set and sensing chemistry for interaction with the analyte. The electrochemical test device may be a monitoring component which transmits an output signal to a separate device such as a meter, either wirelessly or through a wired connection. The electrochemical test device may comprise a continuous monitoring device or a semi-continuous monitoring device.

The electrochemical test device may be suitable for testing for multiple analytes. For example, the conductor layer may comprise a number of working electrodes, each working electrode featuring different sensing chemistry for detecting a different analyte. In particular, for each analyte there may be a dedicated working electrode of the conductor layer coated in a particular reagent suitable for reacting with the analyte.

In the example discussed above in relation to FIG. 2, the electrochemical test device had an end-fill configuration. In other embodiments, an electrochemical test device has a side-fill configuration i.e. the fluid sample is received at the side of the electrochemical test device.

The electrochemical test device may be suitable for measuring any fluid sample volume and may be of a suitable corresponding size for the volume. For example the electrochemical test device described in relation to FIG. 2 was arranged to receive approximately 0.5 μl of blood. The electrochemical test device may be scaled so as to receive other volumes including, for example, between 0.5 μl and 5 μl of a fluid, or between 0.5 μl and 1 μl of a fluid. The electrochemical test device may be scaled so as to receive less than 0.5 μl of a fluid, for example around 0.2 μl or around 0.3 μl.

Although in the discussion above in relation to FIG. 2 a fill-sufficiency detect electrode 218 was present, the fill-sufficiency detector need not be present. Additionally, the fill-sufficiency detector may or may not be coated in one or more reagent layers.

The analyte sensitive layer may be disposed upon the working electrode(s), the working electrode(s) and counter/reference electrode, or the working electrode(s), the counter/reference electrode and the fill-sufficiency detect electrode.

In the examples provided above, the conductor layer and the insulator layer are printed layers. The conductor layer and the insulator layer may be supplied using any suitable manufacturing technique. These include forms of printing, for example, screen printing, lithographic printing or tomographic printing. The conductor layer and the insulator layer need not be provided in the same way. Other suitable manufacturing techniques include etching, and/or sputtering, chemical vapour deposition or physical vapour deposition.

A conductor layer may be formed of any suitable conductor. For example, the conductor layer may be formed from a carbon based paste, such as a carbon/graphite paste, including graphene. The conductor layer may be formed of one or more metal based paste such as a gold, platinum or silver paste. Although the conductor layer 212 described above in relation to FIG. 2 comprises carbon-based ink, the conductors need not be formed from carbon based ink. For example, the electrodes may be formed of silver (Ag) or silver/silver chloride (Ag/AgCl). In some examples, the electrodes are formed of different conducting materials. The working electrode may, for example, be formed of carbon based ink whereas the counter/reference electrode may be formed of silver (Ag) or silver/silver chloride (Ag/AgCl).

The counter/reference electrode may be coated with a layer comprising an electron transfer agent. For example, an electrode formed from carbon based ink may be coated with a layer comprising mediator. The counter/reference electrode may not be coated in any sensing chemistry. For example, sensing chemistry may be absent from a counter/reference electrode formed of silver (Ag) or silver/silver chloride (Ag/AgCl).

The conductor layer may be of any suitable thickness. For example, the conductor layer may have a thickness greater than or equal to 0.005 mm and less than or equal to 0.030 mm.

The insulator layer may be formed of any suitable insulating material. For example, dielectric/insulation inks may be polymer loaded inks that are thermoplastic, thermoset or UV cured and that, when dried or cured, form a contiguous non-conductive layer. Examples include, Loctite EDAG PF 021 E&C and DuPont 5018.

In the examples discussed above, a polyester substrate layer was featured. Suitable substrate materials include polyester, polyimide, polystyrene, PVC, polycarbonate, glass and ceramic. When other layers are to be printed onto the substrate layer, the substrate layer has to be suitably printable for the chosen inks. The substrate must also be non-conductive. Typical thicknesses of the substrate layer range from 0.1 mm to 0.5 mm e.g. 0.35 mm. Glass and ceramic can be thicker as these are easier to handle with increased thickness. Thinner polymer substrates may be more difficult for the end user to use. Thicker substrates may offer some handling benefits.

The spacer layer may be formed of any suitable material. For example, the spacer layer may be made from a polyester core with a thin layer of PSA (Pressure Sensitive Adhesive) on either side. These adhesives can be the same or different depending on which layer is to be adhered to which side of the spacer layer.

Although in the examples above the thickness of the spacer layer was 0.1 mm, the thickness may vary. A typical range for the spacer layer thickness is 0.005-0.030 mm. Lower thicknesses may affect sensor performance and higher thicknesses would increase the volume of the sample introduction channel. A thickness of an adhesive on the spacer layer may contribute to the rigidity of the spacer layer.

Typically a spacer layer has a high volume resistivity. For example the volume resistivity may be greater than $1 \times 10^9$ $\Omega$cm.

Other variations of the spacer layer are envisaged.

The sample introduction chamber may be provided along the longitudinal axis of the electrochemical device. The sample introduction chamber may be provided along the transverse axis of the electrochemical test device.

The vent may be of any suitable configuration for venting air from the sample introduction chamber. For example, the vent may comprise an air passageway in the cover. The vent may comprise an air passageway in the spacer layer. Optionally, air may be vented from the sample introduction chamber through one or more air passageways below the spacer layer, such as through the conductor layer or the insulator layer.

EXAMPLES

Example 1

The NAD(P)H detection layer of an electrochemical test device was prepared as an ink suitable for screen printing using the following formulation:
50 mL 0.1 M Tris buffer, pH 7.4
3% (w/w) hydroxyethyl cellulose (HEC)
1.5% (w/w) silica
0.5% (v/w) Tween 20
10% (w/w) ruthenium pentaammine chloride ([Ru$^{III}$(NH$_3$)$_5$Cl].2Cl)
0.13% (w/w) flavin mononucleotide
0.67% (w/w) diaphorase Example 2

The analyte selective layer for an electrochemical test device was prepared as an ink suitable for screen printing using the following formulation:
75 mL 0.1M Tris buffer, pH 7.4
3% (w/w) HEC
1.5% (w/w) silica
0.5% (v/w) Tween 20
2% (w/w) Nicotinamide adenine dinucleotide (NAD)
1.33% (w/w) β-hydroxybutyrate dehydrogenase (an NAD$^+$-dehydrogenase).

Example 3

Test strips A were prepared using an NAD(P)H detection layer as described in Example 1 and an analyte selective layer as described in Example 2. Test strips B were prepared in an analogous method as test strips A, but using ruthenium hexaammine trichloride as the electron transfer agent in the NAD(P)H detection layer in Example 1.

Test strips A and B were tested in a test meter for 5 seconds using a test voltage at 0.3 V. Samples were tested with varying uric acid concentrations ranging from 0 to 800 μM.

Figure 4:
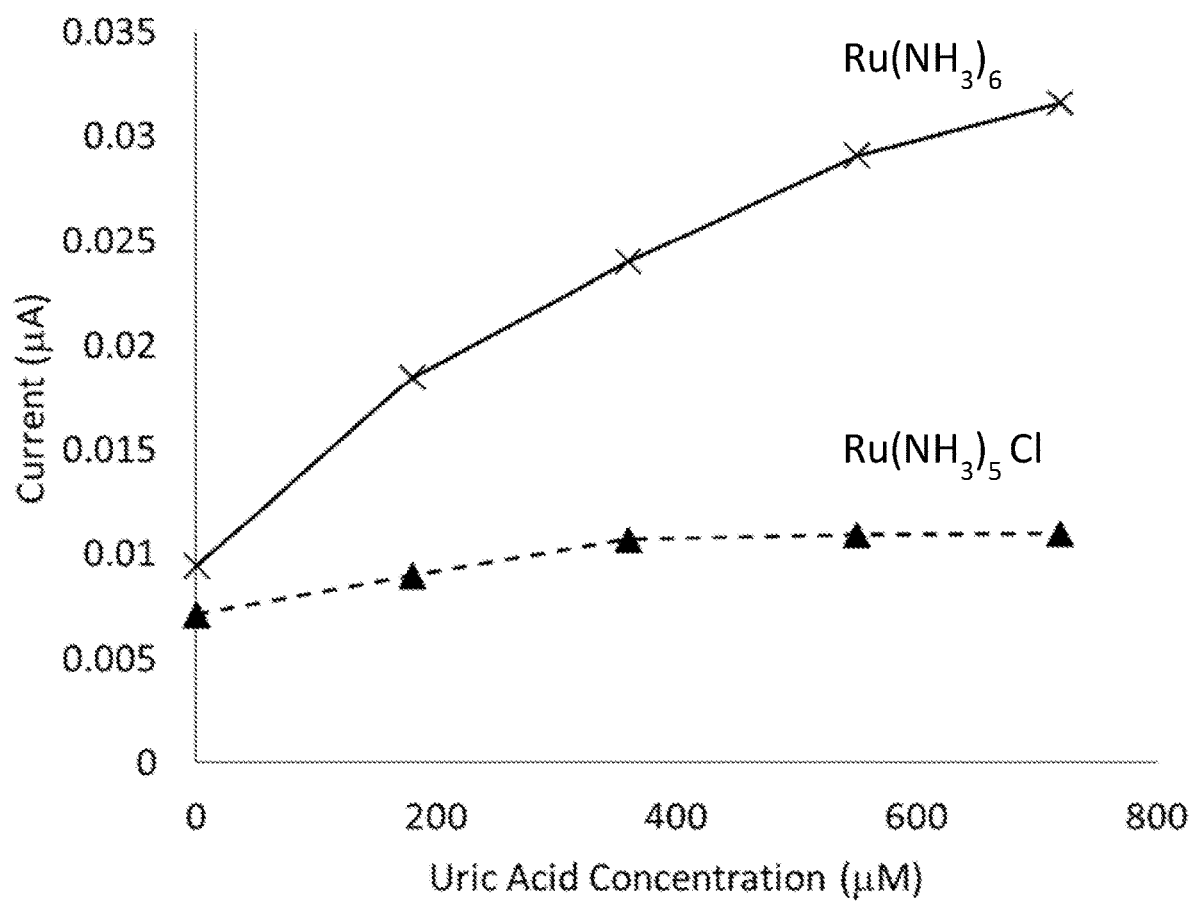
FIG. 4 shows the sensitivity of uric acid for the electrochemical test strips A and B.

FIG. 4 shows the sensitivity of uric acid for the electrochemical test strips A and B. From this data, the relative sensitivities of the two variants of the test strip can be calculated as $3 \times 10^{-11}$ A/μM uric acid for test strips B and $5 \times 10^{-12}$ A/μM for test strips A. This corresponds to a positive bias in the measurement of NADH of:

Test strip A ([Ru(NH$_3$)$_5$Cl].2Cl): $2 \times 10^{-5}$ mM NADH/μM uric acid, which is equivalent to 10 μM NADH for physiological levels of uric acid.

Test strip B ([Ru(NH$_3$)$_6$].3Cl): $7 \times 10^{-5}$ mM/μM uric acid, which is equivalent to 37.5 μM NADH for physiological levels of uric acid.

The test strip A therefore shows that uric acid, which is a potentially interfering compound, was less oxidized by [Ru(NH$_3$)$_5$Cl].2Cl than [Ru(NH$_3$)$_6$].3Cl, which will therefore enable a more selective analyte measurement.

Example 4

Test strips A, for β-hydroxybutyrate analyte, were tested in a test meter for 5 seconds using a test voltage at 0.3 V. Samples were tested with varying β-hydroxybutyrate concentrations ranging from 0 to 4.85 mM.

Figure 5:
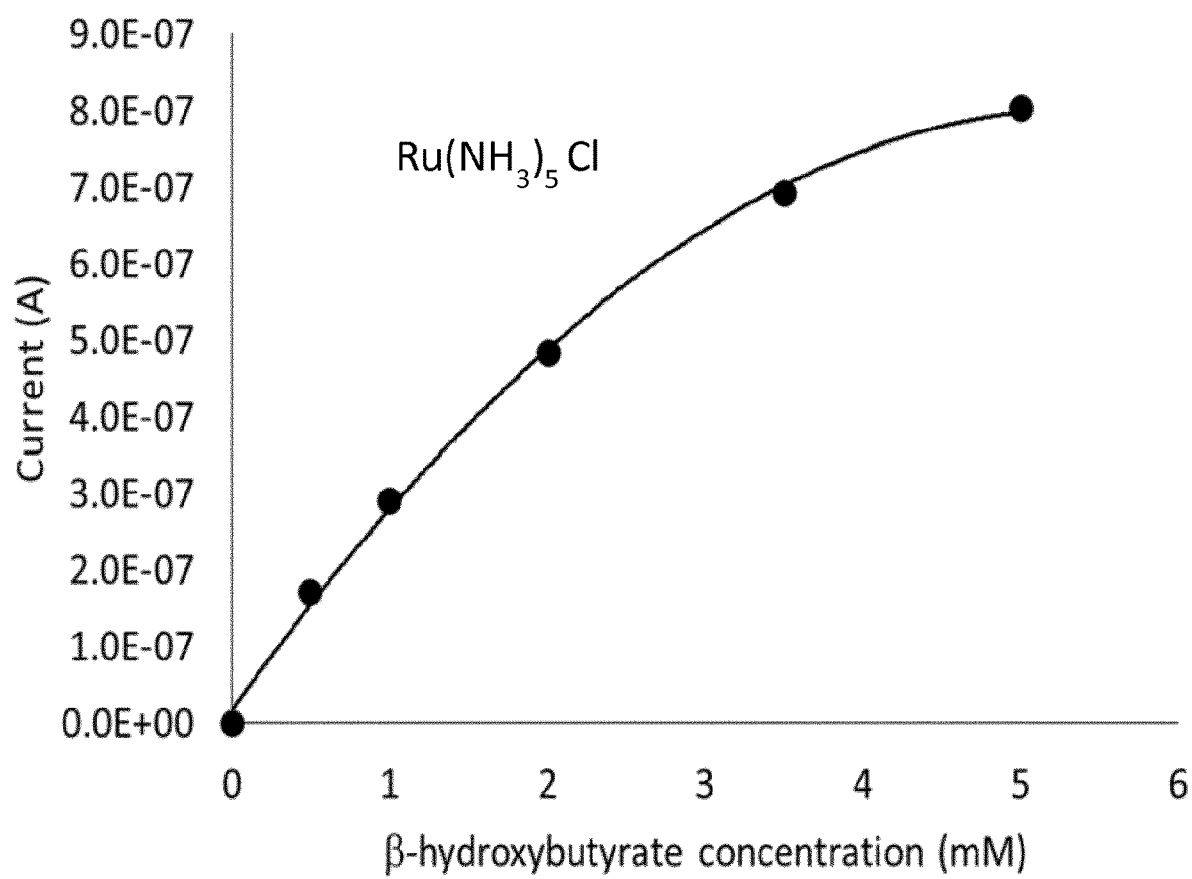
FIG. 5 shows the dose response curve for the detection of β-hydroxybutyrate in whole blood.

FIG. 5 shows the dose response curve for the detection of β-hydroxybutyrate in whole blood with a haematocrit content of 42%.

Example 5

The analyte selective layer for an electrochemical test device was prepared as an ink suitable for screen printing using the following formulation:
20 mL Tris buffer 0.1M pH7.4
3% (w/w) HEC
1.5% (w/w) Silica
0.5% (v/v) Tween 20
10% (w/w) Ruthenium Pentaammine Chloride
1.0% (w/w) Glucose Oxidase Test strips C were prepared using an analyte selective layer as described in Example 5. Test strips C were tested in a test meter for 5 seconds using a test voltage at 0.3 V. Samples were tested with varying glucose concentrations ranging from 50 to 460 mg/dL.

Figure 6:
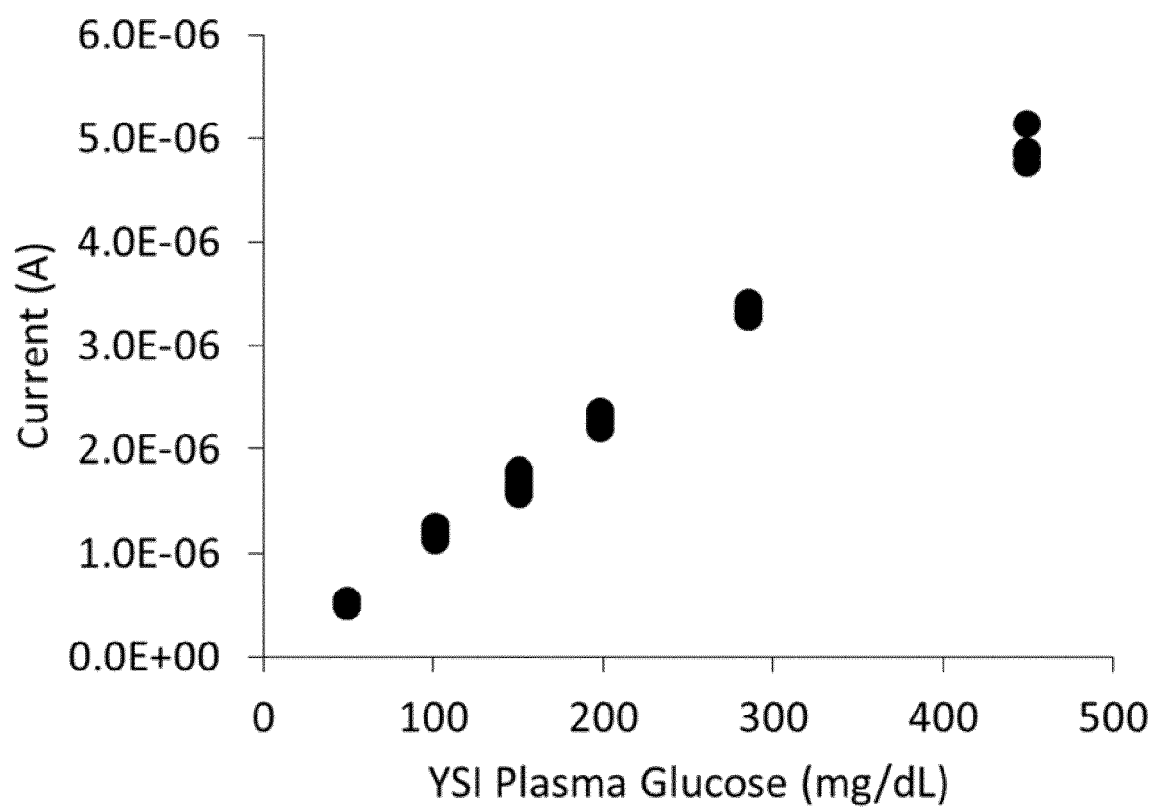
FIG. 6 shows the dose response curve for the detection of glucose in whole blood.

FIG. 6 shows the dose response curve for the detection of glucose in whole blood with 42% haematocrit.

In the disclosure above, an NAD(P)$^+$-dependent dehydrogenase in the analyte selective layer for reacting with an analyte was described for use in conjunction with a diaphorase in the NAD(P)H detection layer. Examples of suitable NAD(P)$^+$-dependent dehydrogenases include Glycerol dehydrogenase, Glycerol-3-phosphate dehydrogenase, D-3-Hydroxybutyrate dehydrogenase, Glucose Dehydrogenase (NAD Dependent), Cholesterol Dehydrogenase, Lactate Dehydrogenase, D-Lactate dehydrogenase, Malate Dehydrogenase, Alcohol Dehydrogenase and Leucine dehydrogenase.

Whilst the above examples have been described primarily in the context of an electrochemical test device for measuring a concentration of an analyte in a bodily fluid, it may equally be used in other fields, for example in health and fitness, food, drink, bio-security applications, veterinary medicine and environmental sample monitoring. The examples described herein may equally be used in the context of animal/veterinary medicine and fitness (including horses and dogs).

Various additional details of aspects of electrochemical test devices are described in the following commonly assigned patent applications (denoted collectively herein as the "related applications". These related applications include the International patent application PCT/GB2016/051230 entitled "Electrochemical test device" filed on 28 Apr. 2016; the International patent application PCT/GB2016/051231 entitled "Electrochemical test device" filed on 28 Apr. 2016; the International patent application PCT/GB2016/051232 entitled "Electrochemical test device" filed on 28 Apr. 2016; the International patent application PCT/GB2016/051229 entitled "Electrochemical test device" filed on 28 Apr. 2016; the International patent application PCT/GB2016/051233 entitled "Electrochemical test device" filed on 28 Apr. 2016; and the International patent application PCT/GB2016/051227 entitled "System and method for measuring fitness-related parameters" filed on 28 Apr. 2016. The content of each of these related applications is hereby incorporated by reference herein in its entirety for all purposes.

The above embodiments have been described by way of example only, and the described embodiments are to be considered in all respects only as illustrative and not restrictive. It will be appreciated that variations of the described embodiments may be made without departing from the scope of the invention.

The invention claimed is:

1. An electrochemical test device for determining a concentration of an analyte in a fluid sample, the electrochemical test device comprising a set of electrodes including a working electrode and sensing chemistry for the working electrode, wherein the sensing chemistry comprises a diaphorase and a ruthenium- or osmium-based electron transfer agent, wherein the ruthenium- or osmium-based electron transfer agent is a complex of formula I:

$$(M(A)_x(B)_y)(X)_n \qquad \text{Formula I}$$

wherein;
M is ruthenium or osmium;
A is an amine ligand;
each B is a ligand different to A;
x is an integer selected from 1 to 5;
y is an integer selected from 1 to 5;
x+y is 6 or 8;
n is an integer selected from 1 to 6;
X is any suitable counterion;
wherein the sensing chemistry is disposed on the working electrode in two layers, further wherein a layer adjacent the working electrode comprises the diaphorase.

2. An electrochemical test device according to claim 1, wherein the sensing chemistry further comprises glucose oxidase.

3. An electrochemical test device according to claim 1, wherein the diaphorase is either NADH dehydrogenase or NADPH dehydrogenase.

4. An electrochemical test device according to claim 1, wherein M is ruthenium.

5. An electrochemical test device according to claim 1, wherein B is halide, or optionally substituted heteroaryl.

6. An electrochemical test device according to claim 5, wherein B is chloride.

7. An electrochemical test device according to claim 1, wherein B is a substituted pyridine.

8. An electrochemical test device according to claim 1, wherein B is pyridine or 4-methyl pyridine.

9. An electrochemical test device according to claim 1, wherein the oxidation state of M is selected to be 2+ or 3+.

10. An electrochemical test device according to claim 1, wherein the ruthenium complex is selected from [Ruthenium$^{III}$(NH$_3$)$_5$(pyridine)]X, [Ruthenium$^{III}$(NH$_3$)$_5$(4-methyl pyridine)]X, and [Ruthenium$^{III}$(NH$_3$)$_5$Cl]X.

11. An electrochemical test device according to claim 1, wherein the counterion X is selected from F$^-$, Cl$^-$, Br$^-$, I$^-$, PF$_6^-$.

12. An electrochemical test device according to claim 1, wherein the ruthenium- or osmium-based electron transfer agent has a standard redox potential in the range of −0.52 to 0.35V.

13. An electrochemical test device according to claim 12, wherein the standard redox potential is in the range of −0.52 to 0.18 V.

14. A composition according to claim 1, wherein the ruthenium- or osmium-based electron agent is a ruthenium-based electron transfer agent, and wherein the concentration of the ruthenium-based electron transfer agent is from 8% to 15% by wt.

* * * * *